US00PP14017P39

(12) United States Plant Patent
Meilland

(10) Patent No.: US PP14,017 P3
(45) Date of Patent: Jul. 22, 2003

(54) FLORIBUNDA ROSE PLANT NAMED 'MEISTADI'

(75) Inventor: Alain A. Meilland, Antibes (FR)

(73) Assignee: CP (Delaware), Inc., Wilmington, DE (US)

( * ) Notice: Subject to any disclaimer, the term of this patent is extended or adjusted under 35 U.S.C. 154(b) by 0 days.

(21) Appl. No.: 09/997,172

(22) Filed: Nov. 30, 2001

(65) Prior Publication Data

US 2002/0148013 P1 Oct. 10, 2002

(30) Foreign Application Priority Data

Apr. 4, 2001 (FR) ..... 17669

(51) Int. Cl.[7] ..... A01H 5/00
(52) U.S. Cl. ..... Plt./141
(58) Field of Search ..... Plt./141, 102, 107, Plt./149

(56) References Cited

U.S. PATENT DOCUMENTS

PP11,025 P * 8/1999 Meilland ..... Plt./123

* cited by examiner

*Primary Examiner*—Howard J. Locker
(74) *Attorney, Agent, or Firm*—Burns, Doane, Swecker & Mathis, L.L.P.

(57) ABSTRACT

A new and distinct variety of rose plant of the Floribunda Class is provided which abundantly forms attractive double purple-violet blossoms that well retain their coloration. The buds are globular in configuration and are borne on strong stems that are capable of supporting a heavy inflorescence. A bushy growth habit is exhibited. The foliage is rather dense and dark green and contrasts nicely with the purple-violet blossoms. The plant is well suited for the production of cut floral sprays under greenhouse growing conditions.

1 Drawing Sheet

Figures 1, 2, 3, 4, 5, 6, 7, 8, 9, 10, 11, 12, 13, 14, 15, 16, 17:
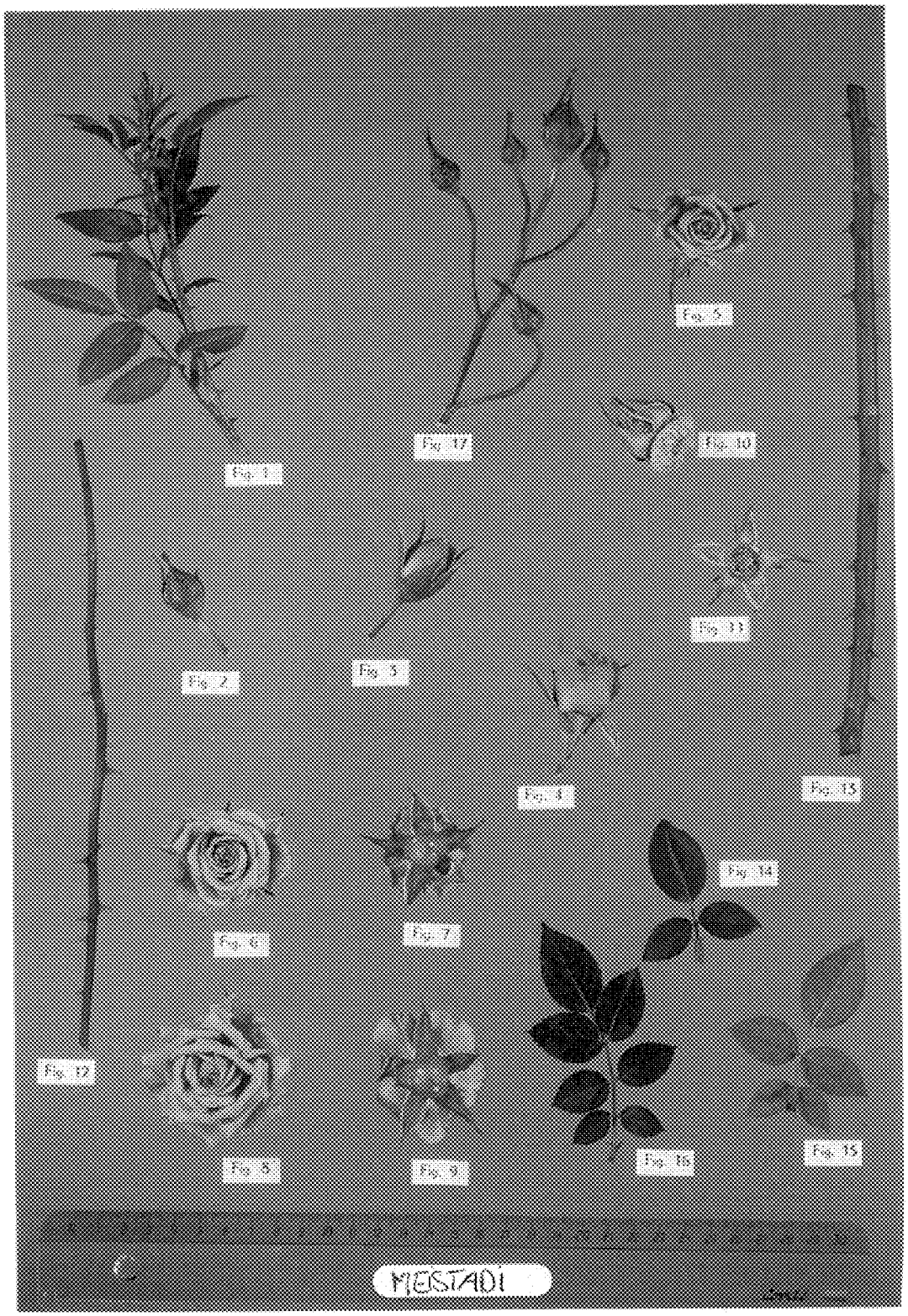

Botancial/commercial classification: Rosa hybrida/Floribunda Rose Plant.
Varietal denomination: cv. 'Meistadi'.

SUMMARY OF THE INVENTION

The new variety of Rosa hybrida floribunda rose plant was created by artificial pollination wherein two parents were crossed which previously had been studied in the hope that they would contribute the desired characteristics. The female parent (i.e., the seed parent) of the new variety was the 'Miebarke' variety (U.S. Plant Pat. No. 6,791). The male parent (i.e., the pollen parent) of the new variety was the product of the cross of the 'Savadream' variety (U.S. Plant Pat. No. 7,757) and the 'Meiptima' variety (U.S. Plant Pat. No. 11,025). The parentage of the new variety can be summarized as follows:

'Meibarke'×('Savadream'×'Meiptima').

The seeds resulting from the above pollination were sown and small plants were obtained which were physically and biologically different from each other. Selective study resulted in the identification of a single plant of the new variety.

It was found that the new variety of floribunda rose plant of the present invention possesses the following combination of characteristics:

(a) forms strong stems that are capable of supporting a heavy inflorescence, (b) displays in abundance attractive double purple-violet blossoms in the form of a spray that retain their coloration well, (c) exhibits a bushy growth habit, and (d) forms attractive rather dense semi-glossy dark green foliage.

The purple-violet spray inflorescence coloration contrasts nicely with the rather dense dark green foliage.

The new variety well meets the needs of the horticultural industry. It is particularly well-suited for use in the production of cut floral sprays under greenhouse growing conditions.

The new variety of the present invention can be readily distinguished from its ancestors. More specifically the 'Meibarke' variety is miniature, forms bicolored red flowers with cream petal margins, and displays a lesser petal number of approximately 15 on average. The 'Savadream' variety also is miniature, forms medium pink flowers, and displays a lesser petal number of approximately 20 on average. The 'Meiptima' variety additionally is miniature, forms lavender flowers, and displays a lesser petal number of approximately 37 to 39 on average.

The new variety has been found to undergo asexual propagation in France by a number of routes, including budding, grafting, and cuttage. Asexual propagation by the above-mentioned methods as performed in France has shown that the characteristics of the new variety are strictly transmissible from one generation to another.

The new variety has been named the 'Meistadi' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age were observed during April while growing on *Rosa indica* understock in greenhouses at LeCannet des Maures, Var, France. Dimensions in centimeters are shown at the bottom of the photograph.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower during the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates a specimen of a leaf with three leaflets—plan view—upper surface;

FIG. 15—illustrates a specimen of a leaf with five leaflets—plan view—under surface;

FIG. 16—illustrates a specimen of a leaf with seven leaflets—plan view—upper surface; and FIG. 17—illustrates a specimen of a cluster of buds.

DETAILED DESCRIPTION

The chart used in the identification of the colors is that of The Royal Horticultural Society (R.H.S. Colour Chart). When more common color terms are utilized they are to be accorded customary dictionary significance. The description is based on two year-old specimens of the new variety which were observed during August while budded on *Rosa indica* understock and growing in greenhouses at LeCannet des Maures, Var, France.

Class: Floribunda.

Plant:

*Height.*—approximately 70 cm when the petals begin to open.

*Width.*—Approximately 50 cm on average.

*Habit.*—Bushy.

Branches:

*Color.*—Young stems: medium green, near Yellow-Green Group 146A. Adult wood: medium green, near Green Group 137B.

*Thorns.*—Size: both long and short prickles commonly are present. Configuration: generally straight on the upper surface and slightly concave on the under surface. Color: on young stems near Grey-Brown Group 199D and slightly suffused with Greyed-Red Group 181D, and near Greyed-Red Group 181D on adult stems. Quantity: on 20 cm of young stems approximately 5 to 6 long prickles greater than 5 mm commonly appear and approximately 12 prickles less than 5 mm commonly appear, and on 26 cm of adult stems approximately 7 to 8 long prickles greater than 5 mm commonly appear and approximately 7 prickles less than 5 mm commonly appear.

Leaves:

*Petioles.*—Slightly glandular, smooth, approximately 0.8 cm in length on average, and the coloration is near Green Group 137B on the upper surface and near Yellow-Green Group 144B on the under surface.

*Stipules.*—Adnate, pectinate, and narrow.

*Leaflets.*—Number: 3, 5 (most often), and 7. Shape: generally elliptic with an acute tip and an obtuse base. Size: the terminal leaflet is approximately 3 to 3.5 cm in length on average and approximately 2 cm in width on average. Texture: smooth and relatively thick. Serration: small and single. General appearance: very dense, dark green, and semi-glossy. Color (young foliage): Upper surface: near Green Group 137C and lightly suffused with anthocyanin coloration of Greyed-Red Group 178B. Under surface: near Yellow-Green Group 147B. Color (adult foliage): Upper surface: near Yellow-Green Group 147A. Under surface: near Yellow-Green Group 147B.

Inflorescence:

*Number of flowers.*—Commonly approximately 2 to 7 per stem and sometimes singly.

*Peduncle.*—Rigid, near Yellow-Green Group 144A in coloration, hairy with tiny prickles, and the length is approximately 4.5 to 5.5 cm on average.

*Sepals.*—Upper surface: tomentose, and near Green Group 138A to 138C in coloration. Under surface: glabrous and near Yellow-Green Group 144A in coloration. Commonly three sepals have weak extensions and two sepals have no extensions.

*Buds.*—Shape: globular. Size: small. Length: approximately 2.5 cm on average. Color: as the calyx breaks near Greyed-Purple Group 186D on the upper surface and near Greyed-Purple Group 186C and 186D on the under surface.

*Flower.*—Form: umbrella-shaped. Diameter: approximately 6 to 7 cm on average. Stem length: flowering stems commonly measure approximately 30 to 45 cm in length. Color (when open): Upper surface: near Greyed-Purple Group 186D. Under surface: near Greyed-Purple Group 186D. Size of petal spot at base: small. Color of petal spot at base: near Yellow-White Group 158B on both surfaces. Fragrance: none. Petal number: approximately 100 on average under normal growing conditions. Petal configuration: wedge-shaped with slight undulation at the opening of the sepals, light reflexing of the margin at the beginning of petal opening, and more pronounced reflexing when petals are fully open. Arrangement: imbricated and commonly without petaloids at the center. Texture: thick petals. Petal drop: good, the petals commonly detach cleanly. Anthers: near Yellow-Orange Group 18A in coloration. Stamen number: approximately 150 on average. Filaments: near Yellow Group 2D in coloration, approximately 0.5 to 0.6 cm in length on average, and regularly arranged around styles. Pollen: moderate in quantity and near Yellow Group 12D in coloration. Pistil number: approximately 90 on average. Stigmas: near Yellow-Orange Group 16D tinted with Red Group 51D. Styles: near Yellow-Orange Group 16D in coloration, and approximately 0.3 to 0.4 cm in length on average. Receptacle: smooth, near Yellow-Green Group 144A in coloration, funnel-shaped, approximately 0.4 cm in length on average and approximately 1.2 cm in width on average. Lasting quality: very long, approximately 20 days on average on the plant, and approximately 12 to 14 days on average when cut and placed in a vase.

Development:

*Vegetation.*—Medium.

*Blooming.*—Abundant and nearly continuous.

*Resistance to diseases.*—Good with respect to Powdery Mildew under standard greenhouse growing conditions.

*Aptitude to bear fruit.*—No hips have been observed to date under greenhouse growing conditions.

*Aptitude to forcing.*—Good.

I claim:

1. A new and distinct variety of floribunda rose plant characterized by the following combination of characteristics:

(a) forms strong stems that are capable of supporting a heavy inflorescence, (b) displays in abundance attractive double purple-violet blossoms in the form of a spray that retain their coloration well, (c) exhibits a bushy growth habit, and (d) forms attractive rather dense semi-glossy dark green foliage;

substantially as herein shown and described.

* * * * *

MESTAD1